United States Patent [19]
Smith

[11] Patent Number: 5,420,508
[45] Date of Patent: May 30, 1995

[54] MEASUREMENT OF MATERIAL COMPOSITION AND PROPERTIES

[75] Inventor: Thomas B. Smith, Atkinson, N.H.

[73] Assignee: Auburn International, Inc., Danvers, Mass.

[21] Appl. No.: 127,258

[22] Filed: Sep. 24, 1993

[51] Int. Cl.⁶ ............................................. G01R 33/20
[52] U.S. Cl. .................................................. 324/307
[58] Field of Search ........................ 324/307, 309, 300

[56] References Cited

U.S. PATENT DOCUMENTS

| | | | |
|---|---|---|---|
| 5,015,954 | 5/1991 | Dechene et al. | 324/307 |
| 5,049,819 | 9/1991 | Dechene et al. | 324/307 |
| 5,302,896 | 4/1994 | Dechene et al. | 324/307 |
| 5,302,897 | 4/1994 | Tache et al. | 324/307 |
| 5,319,308 | 6/1994 | Dechene et al. | 324/307 |

Primary Examiner—Sandra L. O'Shea
Assistant Examiner—Raymond Y. Mah
Attorney, Agent, or Firm—Jerry Cohen; Edwin H. Paul

[57] ABSTRACT

A pulsed NMR analysis system and process comprising an on-line system to extract a sample and establish digitized free induction decay curves (C), from which curve components functions are determined using regression techniques to correlate the curve components to the target nuclei, crystalline or amorphous, and to other material characteristics, such as flow rates in plastic (MI and FRR for polyethylene and MF for polypropylene). The invention makes use of Principal Component Analysis (PCA) for deriving an orthogonal set of explanatory parameters and therefrom a set of vectors wherein collinearity is eliminated by Eigenvalue analysis.

16 Claims, 3 Drawing Sheets

MEASUREMENT OF MATERIAL COMPOSITION AND PROPERTIES

CROSS REFERENCE TO RELATED APPLICATIONS

This application is closely related to U.S. Patent Application filed Oct. 13, 1992, entitled "Real time magnetic resonance analysis with non-linear regression means", U.S. Patent Application filed Nov. 13, 1992, entitled "Apparatus to obtain flow rates in plastics via fixed frequency, pulsed NMR", and U.S. Patent Application filed Apr. 23, 1993, entitled "Thermal control for Sample Under Test in an On-line NMR System". All of these patent applications are of common assignment with this application, and the disclosures of all are hereby incorporated herein by reference, as though set out at length herein.

BACKGROUND OF THE INVENTION

Pulsed NMR techniques are used in instruments for the measurement of the type, property and quantity of lattice bound and free, magnetically active nuclei within a sample. Some of the substances and properties that have been measured by NMR techniques are: moisture, polymers and copolymers, oils, fats, crystalline materials, density and melt indices.

Pulsed NMR uses a burst or pulse of energy that is designed to excite the nuclei of a particular nuclear species of a sample being measured (the protons, or the like, of such sample having first been precessed in an essentially static magnetic field); in other words the precession is modified by the pulse. After the application of the pulse there occurs a free induction decay (FID) of the magnetization associated with the excited nuclei. That is, the transverse magnetization associated with the excited nuclei relaxes back to its equilibrium value of zero. This relaxation produces a changing magnetic field which is measured in adjacent pickup coils. A representation of this relaxation is the FID curve.

The general problem in data analysis of the FID curves and model making in NMR systems is to determine an acceptable modeling equation to predict the desired dependent variable (moisture and oils in foodstuffs or density, MI (melt index) or other such parameters in polyolefins) from the set of explanatory data derived from the Marquardt-Levenberg (M-L) analysis of the FIDs obtained from the NMR measurements. Present theory can suggest that some of the explanatory data will be important (crystalline/amorphous ratios for density, for example), but except for some very simple cases, is unable yet to specify an actual functional relationship among the dependent variables (designated in equations as the 'y's) and the explanatory data (designated the 'x's)

Generally the position taken is that there exists a relationship between the 'x' and 'y' data; but it is unknown. If a relationship does exist, it can probably be represented as a power series expansion of the 'x' data. These are definitely assumptions and may not be true in particular cases, but so far they have led to acceptable results.

The analysis method described in the above related applications is to decompose the FID waveform into a sum of separate time function equations. The coefficients of these equations are derived from the FID by use of a Marquardt-Levenberg (M-L) iterative approximation that minimizes the Chi-squared function—a technique well known in the art. Some of the time function equations found useful are: Gaussians, exponentials, Abragams (Gaussian)*(sin(t))*(1/t), modified Gaussian (Gaussian)*(cos(sqrt(t))) and trigonometric. From these time functions all possible ratios of the amplitude parameters (including Hahn echoes, if present) were formed. These ratios, together with the various waveform time decays (T2's) and the reciprocals of all these (which together form the 'x' data set) were fed into a stepwise statistical modeling program to select those parameters which could best forecast the dependent (the 'y') variable (density, melt index, and the like), and produce a general regression equation to predict the desired parameters. It is not unusual for such an 'x' data set to contain 40 or more parameters. This approach generally gave good results with moisture, oils and density, but had limitations when applied to melt index or flow rate ratios in polyolefins.

Explanatory data used in the above referenced patent applications were essentially first order terms (amplitude ratios, T2's and their reciprocals), and there were indications that modeling the more difficult 'y' data (e.g., MI) required more flexibility in the 'x' data set. To this end, the 'x' data set was expanded to include, in addition to the above, all meaningful cross products of the 'x' data (terms such as $x/x=1$ are excluded, but second order terms such as $x*x$ (x times x) are included). This process can expand the presumed relationship between the "x" and "y" data to the second order, and has been found generally adequate to meet the prediction accuracies required. It is to be understood that expansion beyond the second order may be required in some instances. This technique generates great numbers of potential 'x' explanatory terms (in the order of 1000), and generally requires relatively large 'y' data sets before any meaningful models can be obtained. Fortunately, the generally available statistical techniques can be coerced into dealing effectively with data sets of this size, and much improved results began to appear with the more difficult 'y' terms.

There has been one known problem which was not serious with the relatively small 'x' data sets previously used. This is the problem of high internal correlations among the 'x' data—called multicollinearity. Multicollinearity is a natural feature of the analysis of FID data since, for example, a high density sample of polyethylene has a large crystalline component of the FID, with the result that the amorphous region must be small. Similar correlations exist among most of the other parameters, such as the T2's—the time decays of the FID component curves.

When performing regressions with correlated explanatory variables, the danger exists that the various matrices used in such regression analysis may be nearly singular; the more correlated the 'x' data are, the more nearly singular are the matrices (effectively working with, say, ten variables may yield results equivalent to having only 1 or 2 independent variables). This condition can cause the resulting models to be unstable in the sense that relatively small changes in the 'x' data set can cause extremely large variations in the model coefficients or even in the actual explanatory ('x') terms chosen for the model.

With large numbers of the 'x' parameters associated with the inclusion of second order terms, the problem of multicollinearity can not be ignored. Many of the added second order terms have even higher internal correlations than the original data. Removal of the highly correlated (say correlation coefficients above 0.95) is helpful but the problem still remains. That problem is that while prediction may be acceptable for the calibration data set, the on-line predictions are poor because the model is unstable when used with 'x' data that were not part of the calibration data.

In addition to this problem, we have previously noted that the iterative curve fitting M-L techniques may go awry and produce meaningless results. There is a need to find an efficient test for this condition. In the above referenced patent applications, a Marquardt Reference Ratio (MRR) has had some success in finding these M-L failures. MRR makes use of the fact that there are high correlations among the 'x' data.

It is a principal object of this invention to find an improved test to indicate when the M-L iterative technique has produced an erroneous result.

It is a principal object of the present invention to apply statistical processes to alleviate the instability of prediction model equations due to multicollinearity.

It is a principal object of the present invention to obtain flow rates for plastics, (melt index, melt flow and flow rate ratios for polyethylene and polypropylene) via NMR techniques.

It is yet another object of this invention to relate the type, property and quantity of target nuclei of interest accurately and precisely.

SUMMARY OF THE INVENTION

The present invention comprises a nuclear magnetic resonance analysis system where a pulsed signal excites a sample, and a free induction decay (FID) time signal is received from the sample. The FID is analyzed by a system, and a corresponding method, comprising: means for producing and receiving a free induction decay time signal from a sample of interest, means for decomposing the free induction decay curve into component equations, means for forming potential explanatory variables from the coefficients of the equations, means for selecting an appropriate subgroup of the explanatory variables, means for forming principal components by linear transformation from said explanatory variables, means for forming a model regression equation of said principal components, means for regressing and analyzing, from said model regression equation, the equations corresponding to the true types, properties and quantities for the target nuclei and mass characteristics of sample materials. The above principal component formation provides Eigenvectors and Eigenvalues from which collinearity of the transformed explanatory variables may be determined.

In a preferred embodiment said means for selecting accepts collinearity among the explanatory variables to a correlation up to about 0.99 in order to limit the number of explanatory variables on which PCA will be performed. In other preferred embodiments correlations up to, and including, 1.0 are accepted.

It has been discovered that a statistical technique called Principal Component Analysis (PCA) is helpful when applied to the multicollinearity problem. PCA forms orthogonal (uncorrelated) components from the original data.

In addition it has been discovered that PCA has beneficial effects in the application of the M-L analysis of the FID data, to test that the M-L iterative curve fitting process has yielded useful results. This process comprises forming an Eigenvalue matrix ($\lambda$) of the principal components (of the PCA), and arranging this matrix arithmetically. If one or more of the Eigenvalues in this matrix approaches zero (compared to the other Eigenvalues) multicollinearity is indicated. In a preferred embodiment $1 \times 10^{-3}$ is used as a high limit. A zero or nearly zero magnitude for an Eigenvalue ($\lambda k$) implies that the corresponding Eigenvector ($Zk$) is also approximately equal to zero:

$$Zk = Fk(x1, x2 \ldots xn) = 0,$$

where $Fk$ is the linear transform derived via PCA.

This means that for the calibration set of data, certain combinations of the 'x' data are essentially collinear. It has been found that M-L failures generally do not respect these relationships so that failure of the selected $Zk$'s to be sufficiently close to zero constitutes a test of the M-L fit to the FID. In a preferred embodiment this test is used to determine whether the 'x' values obtained from an M-L iterative process comport with those 'x' values from the calibration set. The $Zk$'s with relatively small Eigenvalues are selected for this test. The selected $Zk$'s are calculated and tested against a three to five sigma limit (such limits having been derived from the calibration data set). Solutions which cause any of the selected $Zk$'s to fall outside this range are rejected as M-L fitting failures.

A good description of PCA is contained in "Regression Analysis by Example", by Chatterjee and Price, John Wiley & Sons, Second Edition, Chapters 7 and 8; in addition, "Ridge Analysis", also found in the reference, may be applicable. These two chapters are incorporated by reference herein as if laid out in full.

If the 'x' data are thought of as vectors, multicollinearity among these 'x' vectors is eliminated by using PCA to determine linear transformations on the original explanatory data such that an equal number of new vectors (called 'z') is generated. These 'z' vectors are uncorrelated with each other, and are orthogonal, and a resulting regression on these 'z' data will be stable. The equations transforming the 'x' data into the 'z' data are determined by Eigenvector analysis of the covariance matrix of the 'x' data. Several commercially available programs can perform this analysis and are well known in the art.

The above objects are met in an NMR system that effects a reliable extraction of free induction decay data in a way that is practical in a wide variety of applications, including industrial. The NMR system is calibrated by measuring known samples of target nuclei and, from the FIDs generated, forming a multi-dimensional, linear or non-linear regression relationship to the types, properties and quantities of target nuclei and then to mass or bulk characteristics of the sample material, e.g. density or flow rates in plastics (melt index, melt flow, flow rate ratio for polyethylene and polypropylene). The FIDs are digitized, and decomposed or transformed into a set of equations for the calibration samples from which a set of explanatory parameters is generated. These parameters are transformed, as discussed above, and ultimately form the basis of a regression function, or model, that is calculated relating the type, property and quantity of target nuclei to the parameters. In order to predict an unknown sample, the FID of the unknown sample is decomposed or transformed as were the known samples, the parameters are calculated and these parameters are used with the linear or non-linear regression function derived from the calibration to determine the type, property and quantity of target nuclei in the unknown sample. In a preferred embodiment, the FID is decomposed into multiple time equations via M-L processes and parameters are calculated for each of these time equations. In another preferred embodiment, the parameters are non-dimensional in order to eliminate concentrations and the like from the measurements.

The present invention may be used to advantage with any number or type of time or frequency functions derived from an FID waveform, including Fourier transform functions.

Other objects, features, and advantages will be apparent from the following detailed description of preferred embodiments taken in conjunction with the accompanying drawing(s) in which:

DETAILED DESCRIPTION OF PREFERRED EMBODIMENTS

In the earlier incorporated by reference patent application an entire, temperature compensated NMR system is described in detail, and only a summary of this apparatus is included below. For needed greater detail please refer to the above incorporated by reference applications.

Figure 1:
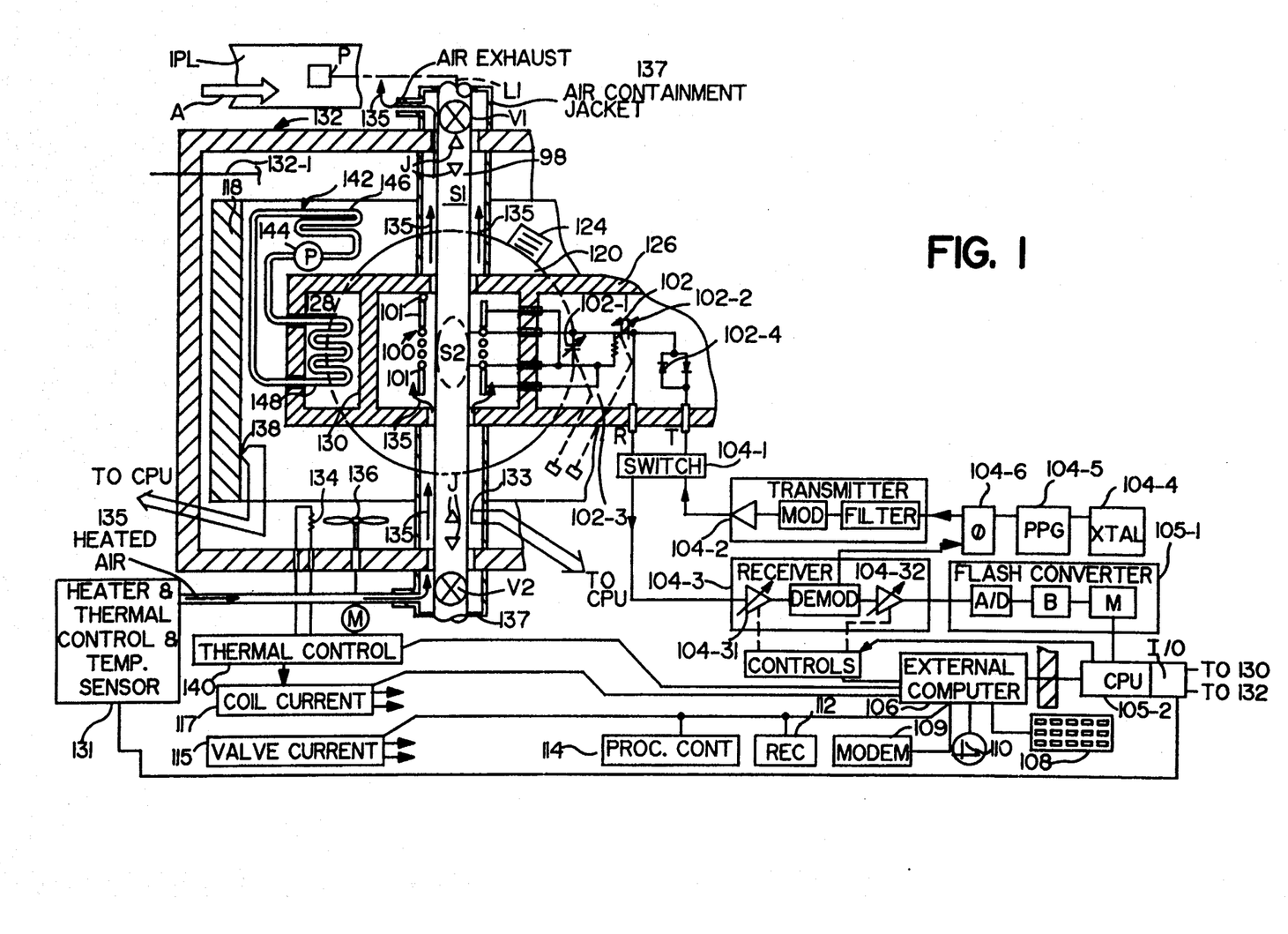
FIG. 1 is a block/schematic drawing of a pulsed NMR system suitable for measuring a range of industrial materials, with an air curtain implementation.

FIG. 1 shows transverse and cross sections with block diagram inserts of an NMR apparatus and method where the present invention may be used to advantage. An industrial process line (IPL) has material flowing as indicated by arrow A. Some of the material is captured by a probe P and fed through an inlet line LI to a critical sample region S2. S2 is surrounded by a sample coil 100 tuned to resonance and driven by a tuning circuit 102 and related transmitter/receiver controller 104. The controller 104 includes an on-board microprocessor and required power supply elements, memory, program and I/O decoding suitable to interconnect to the hardware shown and to an external microcomputer 106 with keyboard 108, monitor (or other display) 110, recorder 112 and/or process controller 114 (to control the process at IPL). The operator initiates and controls operation from the display keyboard 108 and the resulting data and signals are subsequently shown on the display 110 and utilized in 112 and/or 114. The computer 106 also controls instrument operation conditions.

The region S2 is carefully magnetically trimmed and environmentally controlled to maximize the returned signal from the sample. The returned signal is adjusted to be slightly off resonance by about 0.1 to 3 KHz. This returned signal is called a Free Induction Decay time signal or FID curve.

The analog signal FID curve is conditioned to improve signal to noise ratios which enhances the accuracy of the system. The signal is digitized and further digital signal conditioning is done.

The entire curve is decomposed into component curves and these curves are fitted to the data by an iterative process based upon the Marquardt-Levenberg (M-L) approximation technique applied automatically through a realization in software. This technique is used to determine the magnitude of all the parameters, constants, frequencies, etc. which best fit the FID curve. M-L is an iterative technique where the entire curve is determined at once. The M-L iteration process performs the curve fitting by attempting to minimize the Chi-Squared error function (the sum of the squared differences between the measured data points and the data points from the derived equation). The results of the M-L approximation are accepted if the Chi-Squared error is small enough, if not, the M-L fitting procedure may be reapplied with a different set of starting assumptions. If this process also fails, the sample is discarded and a new sample obtained. The M-L technique is documented in the following references: *Ind. Appl. Math.*, vol. 11, pp. 431–441 by D. W. Marquardt, 1963; *Data Reduction and Error Analysis for the Physical Sciences* (New York, McGraw Hill), Chapter 11 by Philip R. Bevington, 1969; and *The State of the Art in Numerical Analysis* (London: Academic Press, David A. H. Jacobs, ed. 1977), chapter III.2 by J. E. Dennis. As applied to the measurement regime of interest herein, in a preferred embodiment of the present invention, the selected parameters taken from the derived curves are the y-axis intercept ratios, time constants, frequency terms and second and higher order combinations of these parameters as described below.

Other known-in-the-art iterative techniques which may be applied instead of or with the Marquardt-Levenberg, include: Gauss-Newton and "steepest descent" (found in the above J. E. Dennis reference), Newton-Raphson (known in the art), partial least squares, or like techniques, including combinations of these techniques. This invention will be used to advantage with virtually any such iterative technique.

One of the major difficulties in making use of iterative curve fitting techniques (such as Marquardt-Levenberg) is their tendency to reach incorrect solutions. Such solutions frequently (but not always) contain parameters which would imply a negative quantity of protons or an exponential "decay" which grows with time. These incorrect solutions lead to serious errors in the result found for a physical sample, for example, the density or flow rates in polyethylene or the extent of tacticity or melt flow in polypropylene.

The usual methods of handling these difficulties have been:

(1) have a human evaluate the result and eliminate those solutions that are theoretically impossible, and/or (2) put a series of upper and lower bounds on each parameter beyond which the fitting procedure is forbidden to go, and (3) MRR described below.

In an on-line situation where readings are generated every few minutes, the first approach obviously cannot be used, and in the case of polyethylene and polypropylene the second approach fails because the bounds for each parameter depend on the actual values of the other parameters, while the third provides some help but has some limitations.

As discussed herein, the techniques to find a property of an unknown sample include calibration by applying the M-L technique to reach solutions for a group of FIDs from samples with known properties. The various amplitudes and time constants in the solutions are combined to produce a number of ratios, cross products and higher order parameters. These parameters undergo various transformations, discussed below, and are finally regressed multidimensionally to obtain the coefficients of the regression equation to use in predicting a property of an unknown sample, say, for example, density. Each of the parameters contributes to the overall prediction of density. However, in the nature of things, these parameters tend to be correlated among themselves; e.g., a large crystalline content must necessarily correspond to a small amorphous content (comparing the modified Gaussian to the exponential in the polyethylene FID solution). This means that overlapping density information is contained in many of the parameters used in the regression equation. Similar arguments apply to other properties, such as tacticity extent or melt flow in polypropylene.

In order to establish effective industrial measurement, a single FID curve is established to see if the sample area is clear (Quick FID) in an abbreviated cycle of attempting to establish a FID curve. If the sample region is not clear (N), measurement is interrupted to allow valve V2 to open and jets J and gravity to clear the region. A new Quick FID step establishes clearance. Then another sample is admitted by closing valve V2, opening valve V1 and making such adjustments of probe P and line L1 as may be necessary to assure sample acquisition. Jets J adjust and stabilize the new sample.

The air curtain described above may be used to establish very coarse and less coarse thermal controls countering sample and ambient temperature variations.

An electronic signal processing apparatus baseline is established in 3-4 cycles (each having (+) and (−) sub-cycles with addition of (C+) and (C−) to detect a baseline offset and compensate for it.

Further adjustment is established by coils 124 to adjust H0 (i.e., resonance) and this is enabled by ten to twenty field check cycles of FID curve generation. The (C−) FID is subtracted from the (C+) FID, (this process eliminates small baseline offsets) to obtain a workable digitized FID signal—which has a maximum value at resonance. H0 is adjusted via coil current generator 117 and coils 124 until such maximum is achieved, and then H0 is changed to offset the system by a given amount of about 0.1 to 3 KHz from resonance.

Then five to one hundred measurement cycles are conducted to obtain a usable measurement. Each of these five to one hundred cycles involves a modulated transmission/reception/flash A-D conversion, and storage of data. The curves are then averaged for noise reduction before M-L curve fitting, M-L is applied and the above listed intercepts and ratios are established. Similar cycles, but somewhat abbreviated can be applied for Quick FID, field check and baseline correction purposes. Each of the sub-cycles [(+) and (−)] of each such cycle involves a capture and utilization of thousands of FID points in data reduction. Each sub-cycle occurs on the order of a second and the number of such sub-cycles employed depends on the desired smoothing and signal to noise ratio (S/N); generally S/N improves in a square root relationship to the number of cycles.

Once the equation of the FID curve is known, each component curve can be extrapolated back to the midpoint of the excitation signal to establish the intercept of each said component curve.

The resulting data utilized in the computer 106 (FIG. 1) is the equation for the FID curve as composed of a number of component curves. Each of these curves (and their intercepts) has been experimentally and theoretically related to particular nuclei of interest. In particular, when the FID curve equation is determined, the ratios of the y-axis intercepts, the cross product and squares of these ratios and the decay times (T2's) for each of the curve components, the product temperature and a cosine term (resonance) form a multidimensional model. These parameters are called explanatory, or 'x', variables in the following discussion.

Calibration of the system is accomplished by measuring a number of known samples and using the M-L technique to derive the model equation constants associated with each known sample. The particular steps of one preferred embodiment are shown in FIG. 2.

Figure 2:
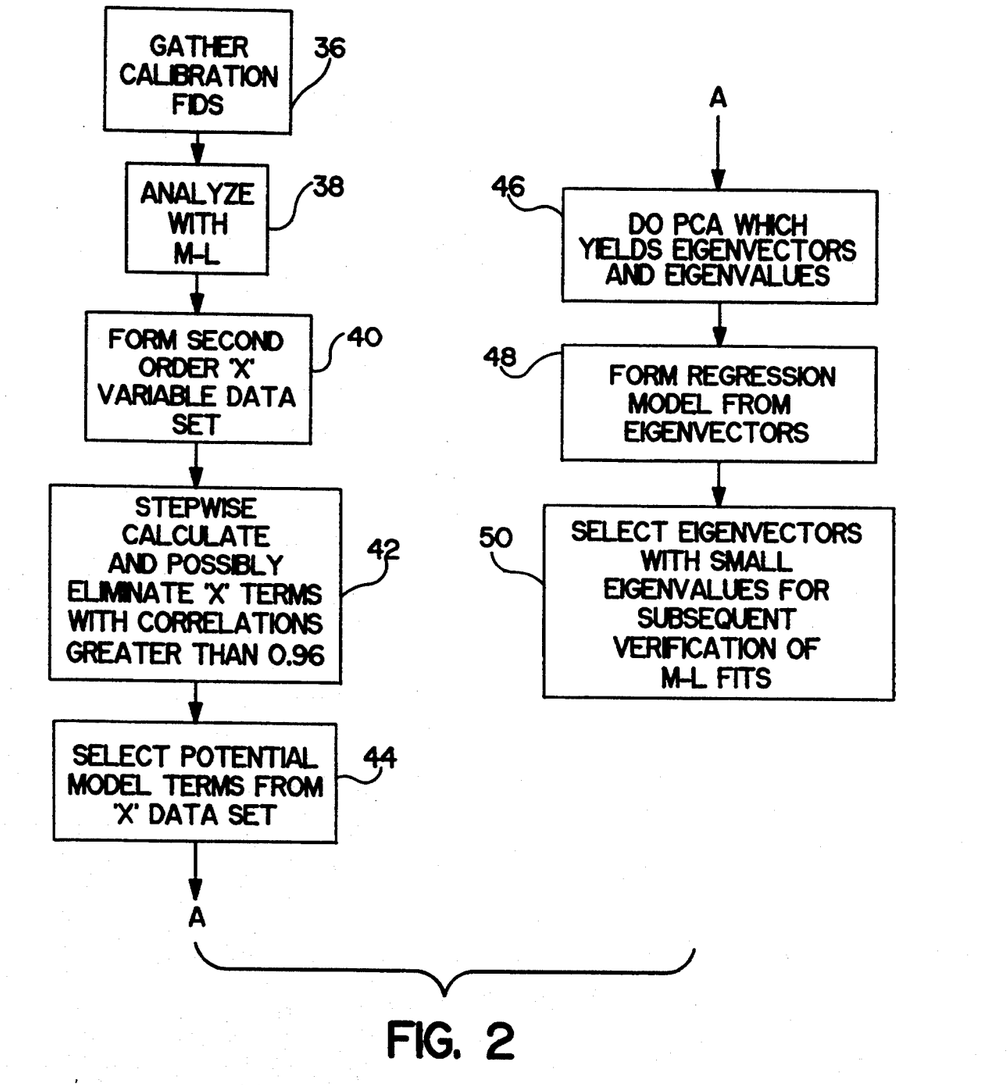
FIG. 2 is a flow chart of the steps to establish an effective industrial measurement model regression equation utilizing the present invention.

Referring to FIG. 2, the first step 36 is to measure samples with known types, properties and quantities of target nuclei, including inherent viscosity, melt index or melt flow (related to average molecular weight) in plastics. This data Gathering may be done on-line or off-line. The FID curve is digitized via a flash converter of at least 12 bits accuracy and stored in computer memory. The next step 38 is to apply the M-L iterative process to derive curve coefficients from the FIDs to a Given Chi-Squared error. In step 40, the second order 'x' variables, the explanatory variables, are formed, e.g., ratios of Y-axis intercepts, squares and cross products of these ratios, decay times, and temperatures. Higher order combinations of these parameters may be calculated. These 'x's can be thought of as vectors in a multidimensional space where the space dimensions are those of the explanatory variables. If there is no multicollinearity among the 'x' data, the vectors are orthogonal in this space (i.e., all dot products are zero). As multicollinearity increases, the vectors move away from orthogonality. In the extreme case there may be perfect correlation between two or more of the 'x' variables and the vectors will lie on top of one another. An attempted regression analysis of such data would generate singular matrices (highly correlated data 44 is eliminated by PCA analysis, described below).

Next a set of potential explanatory variables ('x's) are chosen by stepwise or other known techniques 44. In this preferred embodiment three different sets of 'x' explanatory variables are selected and taken through the entire remaining steps and the set giving the best results is used. In this preferred embodiment the best result is that which results in the lowest adjusted standard deviation of error on the degrees of freedom. One set is composed of all the 'x' variables, the second set is formed by the known stepwise technique of adding each new variable and determining if that variable helped, and then continue adding those variables that help. The techniques is also applied in a backwise fashion where each previously added variable is retested in the presence of each new variable. The third set is formed, by taking all independent variables and variables with correlations against the "y" data between selected low and high limits, usually 0.2 to 0.99 (or higher).

The next step is to perform a principal component analysis (PCA) 46. Potential explanatory variables, the 'x' data, were selected from the M-L derived time equations, including second and higher orders of these variables. As referred to earlier, it is expected that the 'y's (the independent variable) or characteristics of interest of the sample are related by a set of linear or nonlinear equations to these explanatory variables (which may contain high degrees of multicollinearity). However, every regression model can be restated in terms of a set of orthogonal explanatory variables, where these new variables are linear combinations of the original explanatory variables. These new explanatory variables are called principal components. The regression model equation using the original explanatory variables is:

$$Y = X\beta + u,\qquad\text{Eq. 1}$$

where Y is an nx1 column matrix of n observations, X is an nxp matrix of n observations on p explanatory variables, $\beta$ is a px1 column matrix of regression coefficients and u is an nx1 column matrix of residuals. If it is assumed that the expectation of u is 0, and that the expectation of uu' (u' is the conjugate of u) equals the variance times the identity matrix, and that X and Y have been centered and scaled so that the XX' and YY' are matrices of correlation coefficients, then there exists a matrix C, satisfying $$C(XX')C = A,\qquad\text{Eq. 2}$$

and $$C'C = CC' = I,\qquad\text{Eq. 3}$$

where A is a diagonal matrix with ordered Eigenvalues of X'X on the diagonal. The columns of C are the normalized Eigenvalues.

A new set of explanatory variables Z may be formed by Z=XC. These are summarized as:

$$Y = X\beta + u = XCC'\beta + u = Z\alpha + u,\qquad\text{Eq. 4}$$

where the Z vectors are orthogonal.

This process 48 of transforming the 'x' data into 'z' data produces a diagonal matrix C of Eigenvalues of the principal components. The Eigenvector matrix is a square matrix of order n and the scalar is called an Eigenvalue. Eigenvalues may be calculated for matrix A from Eq. 5:

$$|A - \lambda I| = 0,\qquad\text{Eq. 5}$$

where I is the identity matrix.

Those Eigenvalues are sorted numerically from the largest (top left of the diagonal) to the smallest (bottom right). If strong multicollinearity exists, as it does for many of our explanatory variables, one or more of the lower right diagonal terms will be very small compared with the others and these terms may approach zero. If the Eigenvalue is sufficiently close to zero, the value of the corresponding 'z' transform of the 'x' data is also essentially zero:

$$Zk = Fk(x1, x2, \ldots xn) = 0,\qquad\text{Eq. 6}$$

where Fk is the linear transform derived from PCA.

These relationships of Eq. 6 are used to test each M-L curve fit to determine whether the 'x' values obtained from M-L comport with those in the calibration set (derived from the known samples). Those Zk's which have sufficiently small Eigenvalues are selected (as in FIG. 2). A three to five sigma limit on the value of each Zk is used, and M-L solutions which result in Zk's which are outside this range are rejected as M-L fitting failures.

The orthogonal explanatory variables are used in the regression to determine a model equation 48 (referring to FIG. 2). Since the Z variables are orthogonal, step-wise techniques, as described above, are a reliable method for selecting terms for use in the regression model.

Figure 3:
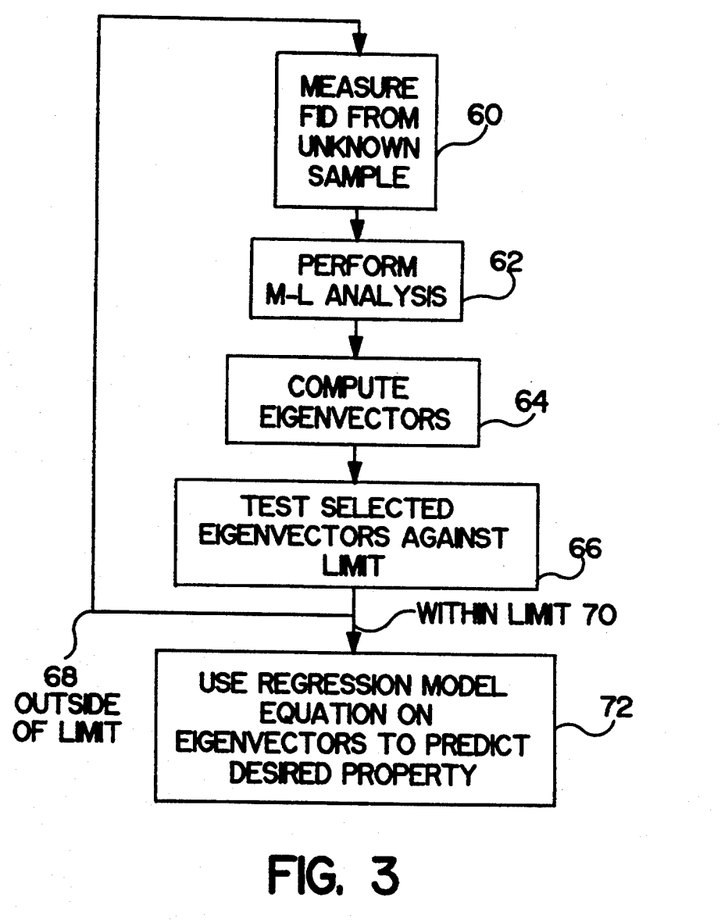
FIG. 3 is a flow chart of the steps to apply the invention to an unknown sample to establish an effective industrial measurement

The calculated regression model equation is applied to an unknown sample via the flow chart of FIG. 3. The FID 60 of the sample is measured and an M-L analysis is performed 62 from which the Eigenvectors are calculated 64. The Eigenvector or Eigenvectors chosen to test the M-L fit are tested against a deviation limitation 66, where the selected vector or vectors divided by the standard deviation(s) of that(those) vector(s) from the calibration data will cause a rejection of the current M-L fit when the result is greater than 3, or in other preferred embodiments greater than 5 or 7. [If outside this limit, M-L 62 is restarted with different starting assumptions and steps 64 and 66 repeated. After repeated failures with a given sample, it is discarded, a new sample is taken, and the steps of FIG. 3 are repeated.]

Still referring to FIG. 3, the Eigenvectors of the M-L solutions which pass the limit test 70 are regressed via the model regression equation to predict the desired property 72.

A PREFERRED EMBODIMENT DESCRIPTIVE SUMMARY

Consider "value" as the property of material to be predicted.

(1) run known samples and gather a statistically significant number of FID's;

(2) analyze these FID's with M-L into component curves;

(3) form a set of variables x (explanatory variables) from these curves;

(4) step-wise reduce the number of x's by: running the entire process for predicting "value" taking the x's one at a time and retaining those x's which improve upon the accuracy of the "value", call this subset x(1);

(5) perform a principal component analysis of the x(1) set which yields a set of independent (orthogonal) variables called z's together with their Eigenvalues;

(6) step-wise (as in (4) above) reduce the z's to a set z(1);

(7) form a regression model equation from z(1);

(8) measure FID from unknown sample;

(9) perform M-L analysis on the sample FID and form the required Z's (the Z1 subset and any z's used for the M-L test);

(10) take the z with the smallest Eigenvalue and test that the sample z is within a limit of 5 (or 3) standard deviations from the calibration z, (after normalization);

(11) if the sample is outside the limit of (10), re-analyze FID via M-L;

(12) if sample within the limits, use regression model equation to predict the desired property.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Nuclear magnetic resonance analysis apparatus comprising:

(a) means for producing and receiving free induction decay signals from a plurality of known samples, (b) means for decomposing said free induction decay signals into calibration component equations, (c) means for forming explanatory variables from said calibration component equations, (d) means for forming principal components by linear transformation from said explanatory variables, and (e) means for forming a regression model equation of said principal components, (f) means for producing and receiving a free induction decay signal from a sample of interest, (g) means for decomposing the sample free induction decay signal of (f) above into component curves and for forming the principal components from said sample signal of (f) above, and (h) means for regressing and analyzing the sample free induction decay signal from said model regression equation to predict the true types, properties and quantities of the target nuclei and mass characteristics of sample materials.

2. Apparatus as defined in claim 1 further comprising:
means for forming Eigenvalues of said principal components generated from said calibration components equations,
means for forming Eigenvalues of said principal components of said sample signals, and
means for comparing said principal components with selected Eigenvalues formed from the calibration and the sample equations and determining therefrom the suitability of the sample component curves for regression.

3. Apparatus as defined in claim 2 wherein the means for comparing is performed on the principal components with the smaller Eigenvalues, and where the standard deviation of the calibration principal component is formed and non-suitability is determined if the principal component value of the sample is more than 3 standard deviations from the calibration value where such non-suitability causes the free induction decay of the sample to be regenerated.

4. Apparatus as defined in claim 1 further comprising:
first means for selecting from said calibration explanatory variables of (c) a subset thereof for use in forming the principal components, and
second means for selecting from said principal components a subset thereof for use in forming the regression model equation.

5. Apparatus as defined in claim 4, wherein the first means for selecting comprises stepwise processes where only explanatory variables which improve prediction are used for forming the principal components, and further wherein the second selecting means comprises stepwise processes where only principal components which improve prediction are used for forming the regression model equation.

6. Apparatus as defined in claim 4 wherein said first means for selecting accepts collinearity of explanatory variables to a correlation of 0.99, or higher.

7. Apparatus as defined in claim 1 wherein said determination of said curve components of said decay curves comprises means utilizing an iteration technique for converting a digitized version of said free induction decay into the time equation of said decay curve and establishing said zero intercepts and time characteristics of said curve.

8. Apparatus as defined in claim 7 wherein said iteration technique comprises a Marquardt-Levenberg technique for converting said digitized version of said free induction decay signals into time equations and establishing zero intercepts and time characteristics thereof.

9. Apparatus as defined in claim 7 wherein said iteration technique comprises a Gauss-Newton technique for converting said digitized version of said free induction decay signals into time equations and establishing zero intercepts and time characteristics thereof.

10. Apparatus as defined in claim 7 wherein said iteration technique comprises a Newton-Raphson technique for converting said digitized version of said free induction decay signals into time equations and establishing zero intercepts and time characteristics thereof.

11. Apparatus as defined in claim 7 wherein said iteration technique comprises a steepest descent technique for converting said digitized version of said free induction decay signals into time equations and establishing zero intercepts and time characteristics thereof.

12. Apparatus as defined in claim 7 wherein said iteration technique comprises a partial least squares technique for converting said digitized version of said free induction decay signals into time equations and establishing zero intercepts and time characteristics thereof.

13. Apparatus as defined in claim 1 wherein means for analyzing the free induction decay components corresponding to types, properties and quantities of target nuclei of the sample materials and flow rates in plastics MI, MF and FRR for polyethylene and polypropylene comprises: means for establishing calibration curves wherein the zero intercepts and time constant characteristics of said decay components of standard samples are related in a regression function to the known physical types, properties and quantities of target nuclei in said standard samples and flow rates in plastics MI, MF and FRR for polyethylene and polypropylene, and means for comparing via said regression function said known sample zero intercepts and time characteristics to the zero intercepts and time characteristics of an unknown sample wherein said physical types, properties and quantities of nuclei of interest and flow rates in plastics (MI, MF and FRR for polyethylene and polypropylene are read from the regression equation.

14. Apparatus as defined in claim 13 wherein said means for comparing said calibration curves to the curve of an unknown sample comprises a non-linear regression analysis.

15. A process for monitoring industrial processes utilizing magnetic resonance comprising the steps of:
(a) producing and receiving free induction-decay signals from a plurality of known samples,
(b) decomposing the free induction decay signals into calibration component equations,
(c) forming explanatory variables from said Calibration component equations,
(d) forming principal components by linear transformation from said explanatory variables,
(e) forming a regression model equation of said principal components,
(f) producing and receiving a free induction decay signal from a sample of interest,
(g) decomposing the sample free induction decay into component curves and for forming the principal components from said sample curves, and
(h) regressing and analyzing the sample free induction decay signal of (f) above from said model regression equation into component curves and forming the principal components from said sample signal of (f) above, and regressing and analyzing the sample free induction decay signal from said model regression equation to predict the true types, properties and quantities of the target nuclei and mass characteristics of sample materials.

16. A process as defined in claim 15 further comprising:

forming Eigenvalues of said principal components generated from said calibration equations, forming Eigenvalues of said principal components of said sample equations, and comparing said principal components formed from the calibration and the sample equations and determining therefrom the suitability of the sample component curves for regression, wherein the comparing is performed on the principal components with the smallest Eigenvalues, and where the standard deviation of the calibration principal component is formed and non-suitability is determined if the principal component value of the sample is more than 3 standard deviations from the calibration value where such non-suitability causes the free induction decay of the sample to be regenerated.

* * * * *